United States Patent
Bariahtaris

(10) Patent No.: US 11,116,814 B2
(45) Date of Patent: Sep. 14, 2021

(54) TURMERIC HEALTH ADDITIVES AND METHODS FOR MAKING SAME

(71) Applicant: Kenneth Bariahtaris, Morristown, NJ (US)

(72) Inventor: Kenneth Bariahtaris, Morristown, NJ (US)

( * ) Notice: Subject to any disclaimer, the term of this patent is extended or adjusted under 35 U.S.C. 154(b) by 263 days.

(21) Appl. No.: 15/989,492

(22) Filed: May 25, 2018

(65) Prior Publication Data

US 2018/0339009 A1    Nov. 29, 2018

Related U.S. Application Data

(60) Provisional application No. 62/511,091, filed on May 25, 2017.

(51) Int. Cl.

| | |
|---|---|
| *A61K 36/9066* | (2006.01) |
| *A23L 33/10* | (2016.01) |
| *A23L 27/10* | (2016.01) |
| *A23L 21/25* | (2016.01) |
| *A23L 5/10* | (2016.01) |
| *A23C 9/133* | (2006.01) |
| *A23C 9/156* | (2006.01) |
| *A61K 47/44* | (2017.01) |
| *A61K 31/12* | (2006.01) |
| *A23L 2/52* | (2006.01) |
| *A23L 33/105* | (2016.01) |
| *A23L 7/143* | (2016.01) |
| *A23L 2/66* | (2006.01) |

(52) U.S. Cl.
CPC .......... *A61K 36/9066* (2013.01); *A23C 9/133* (2013.01); *A23C 9/156* (2013.01); *A23L 2/52* (2013.01); *A23L 5/12* (2016.08); *A23L 21/25* (2016.08); *A23L 27/10* (2016.08); *A23L 33/10* (2016.08); *A23L 33/105* (2016.08); *A61K 31/12* (2013.01); *A61K 47/44* (2013.01); *A23L 2/66* (2013.01); *A23L 7/143* (2016.08); *A23V 2002/00* (2013.01)

(58) Field of Classification Search
CPC ......... A23C 9/133; A23C 9/156; A23L 21/25; A23L 27/10; A23L 2/52; A23L 2/66; A23L 33/10; A23L 33/105; A23L 5/12; A23L 7/143; A23V 2002/00; A61K 31/12; A61K 36/9066; A61K 47/44
See application file for complete search history.

(56) References Cited

U.S. PATENT DOCUMENTS

2010/0119653 A1* 5/2010 Hall ..................... C12Q 1/6883
426/62

OTHER PUBLICATIONS

Torkmahalleh Ma, et al ("Additive impacts on particle emissions from heating low emitting cooking oils" Atmospheric Environment, Aug. 2013, 74, pp. 194-198; doi: 10.1016/j.atmosenv.2013.03.038 (Year: 2013).*
Toden S, Theiss AL, Wang X, Goel A. "Essential turmeric oils enhance anti-inflammatory efficacy of curcumin in dextran sulfate sodium-induced colitis" Sci. Rep., Apr. 11, 2017,7(1):814, 12 pages ; doi: 10.1038/S41598-017-00812-6 (Year: 2017).*

* cited by examiner

*Primary Examiner* — Aaron J Kosar
(74) *Attorney, Agent, or Firm* — Ken Goldman

(57) ABSTRACT

Described herein is a method of making an edible turmeric additive comprising the step of cooking a mixture of turmeric and pepper in a neutral oil.

18 Claims, No Drawings

TURMERIC HEALTH ADDITIVES AND METHODS FOR MAKING SAME

CROSS REFERENCE TO RELATED APPLICATIONS

This application claims priority from U.S. Provisional Application 62/511,091, filed on May 25, 2017.

BACKGROUND

Turmeric (*Curcuma longa*) is a medicinal plant of the genus *Curcuma* belonging to the family Zingiberaceae, and is cultivated in tropical and subtropical regions around the world. Many closely related species of turmeric plants are known. Examples of turmeric plants that are known as ingredients of health food include autumn turmeric, spring turmeric, and purple turmeric. Turmeric rhizome comprises the yellow pigment curcumin. A variety of useful properties of turmeric extracts and curcumin are known, including natural anti-inflammatory and other health benefits. There is a need for improved methods of delivery of turmeric and its extracts, including curcumin, to improve digestive absorption of turmeric into the bloodstream and increase its healthful properties.

SUMMARY

Described herein are methods of preparing turmeric that improve and increase its healthful properties, as well as preparations and foods and beverages utilizing those methods. Without wishing to be held to any particular method of action, it is believed that the methods described herein facilitate digestive absorption of turmeric into the bloodstream, and enhance the taste, texture and appearance of the foods and beverages prepared by these methods.

In one embodiment, there is provided a method of making an edible turmeric additive comprising the step of cooking a mixture of turmeric and pepper in a neutral oil.

In another embodiment, there is provided an edible turmeric additive made by a method comprising the step of cooking a mixture of turmeric and pepper in a neutral oil.

In yet another embodiment, there is provided a method of improving the nutritional health properties of a food or beverage, the method comprising the step of adding an edible turmeric additive to the food or beverage, wherein the additive is made by a method comprising the step of cooking a mixture of turmeric and pepper in a neutral oil.

DETAILED DESCRIPTION

Described herein is a method of making an edible turmeric additive comprising the step of cooking a mixture of turmeric and pepper in a neutral oil.

The turmeric used herein may be turmeric root (or any edible part of the turmeric plant), turmeric spice, turmeric powder, curcumin or a turmeric extract.

Pepper is also used in the methods described herein. The term is intended to include any variety of pepper that includes the alkaloid piperine. Pepper can include black pepper, white pepper, and long pepper (e.g., Balinese long pepper).

In some embodiments, the turmeric-to-pepper ratio in the mixture is between 1:5 and 5:1 by weight. In other embodiments, the turmeric:pepper ratio is about 2:1.

The methods herein also contemplate the optional inclusion of honey when making the additive, primarily for taste. Any type of honey may be used. When honey is used in the mixture, the ratio of honey-to-turmeric is between 1:1 and 5:1 by weight. In some embodiments the honey:turmeric ratio is about 3:1.

The additive is made by cooking or heating the ingredients in a neutral oil. Any known neutral, edible oil may be used in this method. Such oils include flaxseed oil, hemp seed oil, butter, coconut oil, macadamia nut oil, canola oil, walnut oil, extra virgin olive oil, cottonseed oil, grapeseed oil, virgin olive oil, almond oil, hazelnut oil, corn oil, palm oil, palm kernel oil, peanut oil, sesame oil, soybean oil, sunflower oil, olive pomace oil, olive oil, rice bran oil, safflower oil, and avocado oil. In some embodiments, the oil is selected from the group consisting of canola oil, coconut oil, grapeseed oil, sunflower oil, vegetable oil and peanut oil.

The term "cooking", as used herein, is contemplated to mean any known method of heating the additive ingredients in the neutral oil. Typical cooking or heating methods include frying or sauteing the mixture in a non-flammable container (such as a frying pan or similar device) over an open flame, but could also be done in an oven or other heating device.

In some embodiments, the cooking step is performed at a temperature of between 90° C. and 230° C. In other embodiments, the step is performed over a stove at medium low to medium high heat. In still other embodiments, the cooking step is performed for between 5 seconds and 50 seconds. In further embodiments, the cooking step is performed for between 10 seconds and 40 seconds. In yet other embodiments, the cooking step is performed for about between 12 seconds and 15 seconds.

During the cooking step, the mixture may be occasionally stirred to help the ingredients combine properly. The mixture may also be cooked to the point where it thickens slightly.

The mixture, when cooked, is now an edible turmeric additive, which is then ready for direct addition to a food or beverage. Accordingly, in some embodiments, the ratio of mixture-to-oil for the cooking step is between 1:1 and 3:1 by weight. In other embodiments, the mixture:oil ratio is about 2:1.

The edible turmeric additive may be added to a food or beverage, thereby improving the nutritional health properties of the food or beverage. The additive may be added to any food or beverage. In some embodiments, the food or beverage is a dairy or juice product Dairy or juice products include (but are not limited to) smoothies, yogurt, oatmeal or other hot cereal, protein shakes, and milk shakes. In other embodiments, the food or beverage is a yogurt or smoothie.

The proper ratio of the additive to the food or beverage is mostly a function of taste. In some embodiments, this ratio is between 1:10 and 1:40 (by weight). Furthermore, the additive may be added to the food or beverage in any known manner. In some embodiments, the additive is added to the food or beverage by mixing or blending. This method is particularly useful when the food or beverage is a yogurt or smoothie.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

EXAMPLES

Example 1

Edible Turmeric Additive 1 gram of turmeric powder (approx. ½ teaspoon), 3 grams of honey, 0.5 grams of pepper and ½ teaspoon of a neutral oil are combined in a pan on a stove over low/medium heat. As the oil reaches a gentle simmer, the ingredients are stirred to fully combine and very slightly thicken to a consistency between a liquid and a paste. The formation of the final edible turmeric additive takes about 12-15 seconds.

Example 2

Smoothie

The following ingredients: 40-45 grams of ice, 20-25 grams of banana, 30-35 grams of berries (blueberry, blackberry, raspberry, strawberry), ¼ cup of almond/coconut/soy milk, and 20-25 grams of yogurt are combined in a blender along with the additive in Example 1, and blended until the mixture achieves a proper smoothie consistency.

Example 3

Oatmeal/Hot Cereal

⅓ to ½ cup of oatmeal or other hot cereal is prepared per normal cooking directions. The additive as prepared in example 1 is then stirred into the cereal mixture.

Example 4

Yogurt Mixture 40-140 grams of yogurt (approximately 1.5-5 ounces) is stirred or mixed thoroughly with the additive prepared in example 1.

Example 5

Shake (Protein or Milk)

2-10 ounces of a protein or milk shake preparation is stirred, mixed, or blended thoroughly with the additive prepared in example 1.

What is claimed is:

1. A method of improving the nutritional health properties of a food or beverage, the method comprising the step of adding:
   an effective amount of an edible turmeric additive to the food or beverage, wherein the additive is made by a method comprising the step of cooking a mixture of turmeric and pepper in a neutral oil, and
   wherein the food or beverage is selected from the group consisting of a dairy product, a juice product, a yogurt and a smoothie.

2. The method of claim 1 wherein the food or beverage is a dairy or juice product.

3. The method of claim 1 wherein the food or beverage is a yogurt or smoothie.

4. The method of claim 1 wherein the additive:(food or beverage) ratio (wt:wt) is between 1:10 and 1:40.

5. The method of claim 1 wherein the turmeric is a turmeric powder.

6. The method of claim 1 wherein the turmeric is turmeric root or an edible part of the *Curcuma longa* a plant.

7. The method of claim 1 wherein the turmeric:pepper (wt:wt) ratio in the mixture is between 1:5 and 5:1.

8. The method of claim 7 wherein the turmeric:pepper ratio is about 2:1.

9. The method of claim 1 wherein the mixture further comprises honey.

10. The method of claim 9 wherein the honey:turmeric (wt:wt) ratio in the mixture is between 1:1 and 5:1.

11. The method of claim 10 wherein the honey:turmeric ratio is about 3:1.

12. The method of claim 1 wherein the neutral oil is selected from the group consisting of canola oil, coconut oil, grapeseed oil, sunflower oil, vegetable oil and peanut oil.

13. The method of claim 1 wherein the cooking step is performed at a temperature of between 90° C. and 230° C.

14. The method of claim 1 wherein the cooking step is performed over a stove at medium low to medium high heat.

15. The method of claim 14 wherein the cooking step is performed for between 10 seconds and 45 seconds.

16. The method of claim 14 where the cooking step is performed for between 12 seconds and 15 seconds.

17. The method of claim 1 wherein the mixture:oil ratio is between 1:1 and 3:1 (wt:wt).

18. The method of claim 1 wherein the mixture:oil ratio is about 2:1.

* * * * *